United States Patent
Meng et al.

(10) Patent No.: US 11,214,553 B2
(45) Date of Patent: Jan. 4, 2022

(54) METHOD FOR PREPARING 1,4,7,10-TETRAAZACYCLODODECANE-1,4,7,10-TETRAACETIC ACID

(71) Applicant: VIWIT PHARMACEUTICAL CO., LTD., Shandong (CN)

(72) Inventors: Zhoujun Meng, Shandong (CN); Yigang He, Shandong (CN); Yanjun Wei, Shandong (CN); Yanping Xing, Shandong (CN)

(73) Assignee: VIWIT PHARMACEUTICAL CO., LTD., Shandong (CN)

( * ) Notice: Subject to any disclaimer, the term of this patent is extended or adjusted under 35 U.S.C. 154(b) by 97 days.

(21) Appl. No.: 16/473,242

(22) PCT Filed: Sep. 18, 2017

(86) PCT No.: PCT/CN2017/102056
§ 371 (c)(1),
(2) Date: Jun. 24, 2019

(87) PCT Pub. No.: WO2018/120923
PCT Pub. Date: Jul. 5, 2018

(65) Prior Publication Data
US 2020/0347023 A1    Nov. 5, 2020

(30) Foreign Application Priority Data
Dec. 30, 2016 (CN) .......................... 201611262335.6

(51) Int. Cl.
*C07D 257/02*    (2006.01)

(52) U.S. Cl.
CPC .................................. *C07D 257/02* (2013.01)

(58) Field of Classification Search
CPC .................................................. C07D 257/02
USPC ........................................................ 514/183
See application file for complete search history.

(56) References Cited

U.S. PATENT DOCUMENTS

| 5,922,862 A | 7/1999 | Murru et al. |
| 10,195,295 B2 * | 2/2019 | Buffel ...................... C07F 5/003 |

FOREIGN PATENT DOCUMENTS

| CN | 104169252 A | 11/2014 | |
| CN | 104447598 A | 3/2015 | |
| WO | 9905128 A | 2/1999 | |
| WO | 2012142702 A1 | 10/2012 | |
| WO | 2013076743 A | 5/2013 | |
| WO | 2014114664 A | 7/2014 | |
| WO | 2015117911 A | 8/2015 | |
| WO | WO-2015117911 A1 * | 8/2015 | ............. A61K 47/18 |

OTHER PUBLICATIONS

Extended European Search Report issued in the counterpart European patent application No. 17889406.9 dated Nov. 20, 2019.
Fengcheng Wu et al., "Novel polyazamacrocyclic receptor decorated core-shell superparamagnetic microspheres for selective binding and magnetic enrichment of palladium: Synthesis, adsorptive behavior and coordination mechanism", Dalton Transactions, 2016, vol. 45, No. 23, p. 9553-9564.
H. Stetter et al., "Complex formation with tetraazacycloalkane-N,N',N'',N'''-tetraacetic acids as a function of ring size", Angewandte Chemie International Edition in English, vol. 15, No. 11, 1976, pp. 686.

(Continued)

*Primary Examiner* — Rita J Desai
(74) *Attorney, Agent, or Firm* — Liangang Ye; Houston Beshining Law Office PLLC

(57) ABSTRACT

Disclosed is a method for preparing 1,4,7,10-tetraazacyclododecane-1,4,7,10-tetraacetic acid (DOTA) of formula (II), comprising the following steps: carrying out an alkylation reaction on cyclen in formula (I) and $XCH_2COOR$ in the presence of an acid-binding agent in water; adjusting a pH value to separate out a crude product of DOTA; and recrystallizing. The preparation method of the present invention is applicable to large-scale industrial production of DOTA, the whole process does not need to adopt an ion-exchange resin or low-temperature refrigeration mode for purification, and the purity and yield of the product are higher.

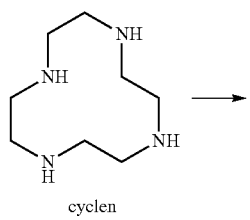

cyclen

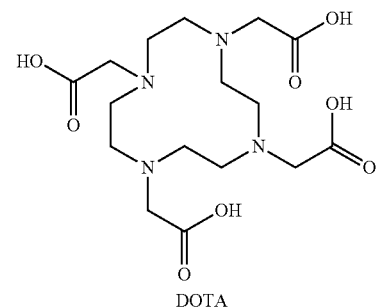

DOTA

18 Claims, 1 Drawing Sheet

(56) References Cited

OTHER PUBLICATIONS

R. Delgado et al., "Metal complexes of cyclic tetra-azatetra-acetic acids", Talanta, vol. 29, issue 10, 1982, pp. 815-822.
E.T. Clarke et al., "Stabilities of the alkaline earth and divalent transition metal complexes of the tetraazamacrocyclic tetraacetic acid ligands". Inorganica Chimica Acta, vol. 190, No. 1, 1991, pp. 27-36.
J. F. Desreux, "Nuclear magnetic resonance spectroscope of lanthanide complexes with a tetraacetic tetraaza macrocycle. Unusual conformation properties", Inorganic Chemistry, vol. 19, No. 5, 1980, pp. 1319-1324.
International Search Report and Written Opinion of PCT/CN2017/102056 dated Dec. 22, 2017.
Apr. 20, 2021 Japanese Notice of Reasons for Refusal issued in Japanese Patent Application No. 2019556400.

* cited by examiner

METHOD FOR PREPARING 1,4,7,10-TETRAAZACYCLODODECANE-1,4,7,10-TETRAACETIC ACID

The present application is a National Stage of International Application No. PCT/CN2017/102056, filed on Sep. 18, 2017, which claims priority of the Chinese Patent Application No. CN201611262335.6 filed on Dec. 30, 2016, the contents of which are incorporated herein by reference in their entireties.

FIELD OF INVENTION

The present invention relates to a method for preparing 1,4,7,10-tetraazacyclododecane-1,4,7,10-tetraacetic acid.

PRIOR ARTS 1,4,7,10-Tetraazacyclododecane-1,4,7,10-tetraacetic acid (DOTA) is an important chemical intermediate and pharmaceutical intermediate, the structure of which is shown in the following formula.

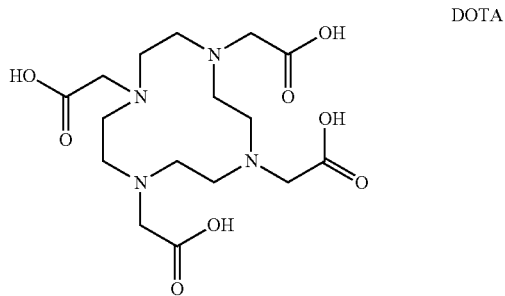 [SMILES: O=C(O)CN1CCN(CC(=O)O)CCN(CC(=O)O)CCN(CC(=O)O)CC1]

DOTA

In 1976, Stetter Hermann and Wolfram Frank first reported on the synthesis of DOTA (*Angewandte Chemie International Edition in English* 15(11): 686) by the reaction of 1,4,7,10-tetraazacyclododecane (cyclen) with chloroacetic acid in an alkaline medium, followed by purification by Dowex-2×8 ion exchange resin to remove inorganic salts to obtain a qualified product.

In 1980, JF Desreux used sodium hydroxide as a base, wherein the reaction temperature was 80° C., and then the pH value was adjusted to 2.5 by acidification to obtain the product, and DOTA was purified by Dowex 50W-X4 ion exchange resin (*Inorg. Chem.* 1980, 19, pp. 1319-1324.).

In 1982, R. Delgado synthesized DOTA by controlling the pH value of alkaline medium at 10 (*Talanta*, Vol. 29, pp. 815-822, Issue 10, 1982), and then the pH value was adjusted to 2 with hydrochloric acid to obtain the product by freezing, which did not involve a purification step.

In 1991, Clarke and A. Martel (*Inorganica Chimica Acta*, 190, pp 27-36) carried out the reaction between cyclen and bromoacetic acid in the pH value range of 11.2-11.3, wherein, after the salts were removed by the ion exchange resin, the filtrate was concentrated, and the pH value was adjusted with hydrochloric acid, followed by purification by recrystallization in hot water to obtain the product.

In WO9905128A1, alkylation and hydrolysis were carried out under alkaline conditions using bromoacetic acid or chloroacetic acid and the respective esters thereof, and the obtained product was purified by ion exchange resin to obtain high-quality DOTA.

U.S. Pat. No. 5,922,862 disclosed a method for purifying the crude product of DOTA and cyclen derivatives, wherein the crude product was dissolved in water and purified by PVP ion exchange resin.

WO2013076743 disclosed that DOTA, diethylenetriaminepentaacetic acid (DTPA), D03A-butrol, BOPTA were adjusted to the pH value to 0.75 with acid to obtain the hydrochloride salts, followed by recrystallization to remove the inorganic salts, and the pH value was adjusted to 1.5-3.0 by A26 OH ion exchange resin and concentrated to obtain the respective product.

WO2014114664A1 disclosed a method for synthesizing and purifying DOTA and the salts thereof, wherein, the of DOTA was synthesized by the reaction between cyclen and an alkylating agent (bromoacetic acid, chloroacetic acid, iodoacetic acid) at a pH value more than 13. After completion of the reaction, the pH value was adjusted to 3 or less with acid, and the crude product was obtained by heating and cooling. Different types of ion exchange resins were used for the purification to obtain high-quality products, and HPLC and IC methods were used for carrying out the process monitoring and product analysis of DOTA.

WO2015117911A1 disclosed a method for purifying DOTA, wherein, the crude product was synthesized according to the techniques reported in the literature, and then purified by nanofiltration to obtain the respective product.

Through the analysis and summary of the above literatures and patents, in the prior techniques of DOTA synthesis and purification methods, the synthesis steps are basically similar, and basically there are three purification methods. First, the purification step uses ion exchange resin, the disadvantages of which are the requirement of concentrated water removal operation in the subsequent process, the requirement of the pretreatment and activation of the ionic resins, and the high consumption of energy and time in the later concentration process. Second, high-quality DOTA product is obtained by low-temperature freezing method, and the temperature requirement is relatively strict, and the operation is not easy. Third, it is difficult for typical enterprises to implement non-generic technology purification, such as nanofiltration technology.

Content of the Present Invention

The technical problems to be solved in the present invention is to overcome the problems of the processes for preparing 1,4,7,10-tetraazacyclododecane-1,4,7,10-tetraacetic acid (DOTA) in the prior art involve the requirement of the pretreatment and activation of the ionic resins, the requirement of concentrated water removal operation in the subsequent process and the high consumption of energy and time in the concentration process, or high temperature requirements and the complex operation, or the requirement of the non-generic technology such as nanofiltration technology. The present invention provides a method for preparing DOTA, which is suitable for large-scale industrial production, and the whole process does not need to be purified by ion exchange resins and low-temperature freezing, and the yield and purity of the product are high.

The present invention solves the above technical problems through the following technical solutions.

The present invention provides a method for preparing 1,4,7,10-tetraazacyclododecane-1,4,7,10-tetraacetic acid (DOTA), which comprises the following steps: carrying out an alkylation reaction on 1,4,7,10-tetraazacyclododecane (cyclen) and $XCH_2COOR$ in the presence of an acid-binding agent in water; adjusting a pH value to precipitate a crude product of DOTA; and recrystallizing;

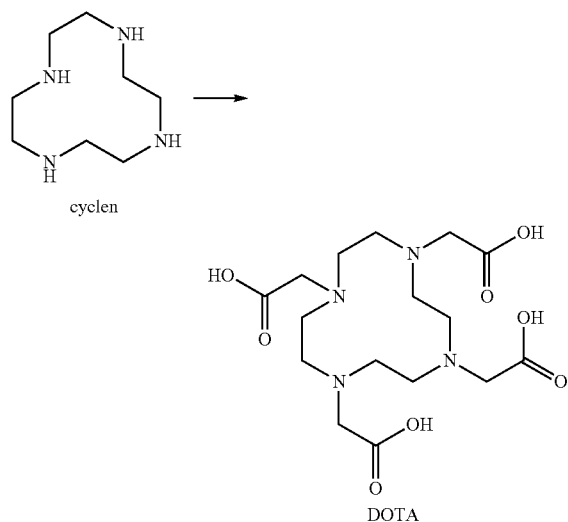

cyclen

DOTA

Wherein, the acid-binding agent is an acid binding agent conventionally used in such alkylation reaction in the art, and the acid-binding agent of the present invention is preferably selected from the group consisting of an alkali metal hydroxide, an alkaline earth metal hydroxide, a carbonate, a bicarbonate, a phosphate, an organic acid salt, an alkoxide and an organic amine. Wherein, the alkali metal is preferably lithium, sodium, potassium, rubidium, cesium, or francium; and the alkaline earth metal is preferably strontium, magnesium, calcium, strontium, barium, or radium.

In the present invention, the acid-binding agent is further preferably selected from the group consisting of an alkali metal hydroxide, an alkali metal carbonate, an alkali metal bicarbonate, an alkali metal phosphate, an alkali metal organic acid salt, an alkali metal alkoxide, and an organic amine; further more preferably selected from the group consisting of an alkali metal hydroxide, an alkali metal carbonate, an alkali metal organic acid salt, and an organic amine. Wherein, the alkali metal hydroxide is preferably selected from the group consisting of lithium hydroxide, sodium hydroxide, potassium hydroxide, rubidium hydroxide and cesium hydroxide; the alkali metal carbonate is preferably selected from the group consisting of lithium carbonate, sodium carbonate, potassium carbonate, rubidium carbonate and cesium carbonate; the alkali metal organic acid salt is preferably an alkali metal acetate, further preferably selected from the group consisting of lithium acetate, sodium acetate and potassium acetate; the organic amine is preferably triethylamine and/or diisopropylethylamine.

In the present invention, the acid-binding agent is further preferably selected from the group consisting of lithium hydroxide, sodium hydroxide, potassium hydroxide, sodium carbonate, potassium carbonate and sodium acetate; further more preferably lithium hydroxide.

In the present invention, when a hydrate of the acid binding agent is stably present, the acid binding agent can also be involved in the reaction in a hydrate form thereof, for example, lithium hydroxide monohydrate.

In the present invention, an amount of the acid-binding agent is preferably such that the pH value of the reaction system is 10-14 after the acid-binding agent is added to the reaction system. Preferably, a molar ratio of the acid-binding agent to the cyclen is 8.0:1 to 10.0:1; further preferably 8.4:1 to 9.2:1, for example, 8.8:1.

In the present invention, the $XCH_2COOR$ is used as an alkylating agent of the alkylation reaction, wherein R is H, an alkali metal or a $C_1$-$C_6$ alkyl; X is chlorine, bromine or iodine. Wherein, the alkali metal is preferably lithium, sodium or potassium; the $C_1$-$C_6$ alkyl is preferably a $C_1$-$C_4$ alkyl, further preferably methyl, ethyl, n-propyl, isopropyl, n-butyl, isobutyl or tert-butyl.

In the present invention, the $XCH_2COOR$ is further preferably selected from the group consisting of chloroacetic acid, bromoacetic acid, iodoacetic acid, sodium chloroacetate, sodium bromoacetate and sodium iodoacetate; further more preferably bromoacetic acid.

In the present invention, an amount of the $XCH_2COOR$ can be a conventional amount for such alkylating agent in the art; a molar ratio of the $XCH_2COOR$ to the cyclen of the present invention is preferably 4.0:1 to 5.0:1; further preferably 4.2:1-4.6:1, for example, 4.4:1.

In the present invention, the $XCH_2COOR$ is preferably formulated into an aqueous solution, and then added to the above reaction system; further preferably formulated into an aqueous solution having a molar concentration of 12.0-18.0 mol/L (e.g., 14.7 mol/L), and added to the above reaction system. The water in the aqueous solution of $XCH_2COOR$ is preferably deionized water. That is, in a preferred embodiment of the present invention, the $XCH_2COOR$ is preferably involved in the reaction in the form of an aqueous solution of $XCH_2COOR$.

In the present invention, the alkylation reaction is carried out in water; preferably deionized water.

In the present invention, an amount of the water is not specifically limited as long as it does not affect the progress of the reaction. A molar concentration of the cyclen of the present invention is preferably 0.5-1.5 mol/L, and more preferably 0.9 mol/L-1.0 mol/L. The molar concentration of the cyclen refers to the ratio of the amount of the substance cyclen to the volume of the cyclen aqueous solution.

In the present invention, when $XCH_2COOR$ is involved in the reaction in the form of an aqueous solution, unless otherwise specified, an amount of water refers to the sum of the volume of water added separately and the volume of water in the $XCH_2COOR$ aqueous solution.

In the present invention, the reaction temperature of the alkylation reaction is conventionally used in the art for carrying out such reaction; preferably −10° C. to 60° C.; further preferably 5-50° C.; further more preferably 20-30° C.

In the present invention, the progress of the alkylation reaction can be monitored by a conventional detection method in the art, such as thin layer chromatography (TLC), gas chromatography (GC), nuclear magnetic resonance spectroscopy (NMR) or high performance liquid chromatography (HPLC), etc.; preferably by TLC or HPLC. When TLC is used as the detection method, the end point of the reaction is preferably the disappearance of the cyclen. When HPLC is used as the detection method, the end point of the reaction is preferably that the cyclen in the reaction system is no longer involved in the reaction or its concentration is less than 0.5%. The percentage used herein refers to the mass percentage of the mass of the cyclen to the total mass of the reaction mixture after the end of the reaction.

In the present invention, the reaction time of the alkylation reaction is preferably from 12 to 24 hours.

In the present invention, the addition order of the reactants for the alkylation reaction can be conventionally used in the art for such reaction. Preferably, the cyclen, the acid-binding agent, the water and the $XCH_2COOR$ are sequentially added to the reaction system; further preferably, the cyclen, the acid-binding agent and the water is added at 0-10° C.; the XCH$_2$COOR or the aqueous solution thereof is added at 5-15° C.

In the present invention, the operation of adjusting the pH value for the precipitation of the crude product of DOTA can be carried out by a conventional post-treatment of such alkylation reaction in the art. The type or the amount of the pH value regulator, pH adjustment method or pH monitoring method is not specifically limited.

Wherein, preferably, the pH adjustment method of the present invention is to add a value regulator to the reaction system; preferably, pH monitoring method is monitored by using a pH meter.

In the present invention, the operation of adjusting the pH value for the precipitation of the crude product of DOTA is preferably method (1) or method (2) as follows:

The method (1) comprises the following steps: after the completion of the alkylation reaction, adding an acidic pH value regulator to adjust the pH of the reaction system for the complete precipitation of the crude product of DOTA acid salt; and then dissolving it in water; adding alkaline value regulator to adjust the pH value of the reaction system for complete precipitation of the crude product of DOTA.

Wherein, the acidic pH value regulator can be a conventional acidic pH value regulator in the art. The acidic pH value regulator of the present invention is preferably selected from the group consisting of hydrochloric acid, hydrobromic acid, hydroiodic acid, nitric acid and sulfuric acid; further preferably hydrochloric acid; further more preferably, 36% w/w aqueous hydrochloric acid solution. In the present invention, it is preferred that the acidic pH value regulator is used in an amount sufficient to lower the pH value of the reaction system to 1 or even below 0.5, thereby completely converting the product of the alkylation reaction (completely deprotonated DOTA) to the fully protonated DOTA acid salt for the complete precipitation from the reaction system.

Wherein, the alkaline pH value regulator can be a conventional alkaline pH value regulator in the art. The alkaline pH value regulator of the present invention is preferably selected from the group consisting of ammonia hydroxide, triethylamine and triisopropylamine; further preferably triethylamine. In the present invention, it is preferred that the alkaline pH value regulator is used in an amount sufficient to adjust the pH value of the reaction system close to the isoelectric point of DOTA (preferably 2.0-4.0, more preferably 3.0-4.0 in the present invention), thereby completely converting the DOTA acid salt to free DOTA for the complete precipitation from its aqueous solution.

The method (2) comprises the following steps: after the completion of the alkylation reaction, adding an acidic pH value regulator to adjust the pH value of the reaction system for the complete precipitation of the crude product of DOTA.

In the method (2), the acidic pH value regulator can be a conventional acidic pH value regulator in the art for pH adjustment of an aqueous phase. The acidic pH value regulator of the present invention is preferably selected from the group consisting of hydrochloric acid, hydrobromic acid, hydroiodic acid, nitric acid and sulfuric acid; further preferably hydrochloric acid; further more preferably, 36% w/w aqueous hydrochloric acid solution. In the present invention, it is preferred that the acidic pH value regulator is used in an amount sufficient to adjust the pH of the reaction system close to the isoelectric point of DOTA (in the present invention, preferably 2.0-4.0, more preferably 3.0-4.0), thereby completely converting the product of the alkylation reaction (completely deprotonated DOTA) to free DOTA for the complete precipitation therefrom. In the present invention, it is further preferred that a molar concentration ratio of the hydrogen proton in the acidic pH value regulator to the cyclen is 4.4:1, or the molar concentration ratio of the hydrogen proton in the acidic pH value regulator to the acid-binding agent is 1:2.

In the method (2), the crude product of DOTA obtained by the above post-treatment can be collected by a conventional treatment method for such reaction in the art. In the present invention, it is preferred to add an organic solvent to precipitate the crude product of DOTA, and the organic solvent is further preferably selected from methanol, ethanol, isopropanol, tetrahydrofuran, acetone and acetonitrile; further more preferably methanol and/or ethanol. An amount of the organic solvent can be a conventional amount for such reaction in the art. In the present invention, it is preferred that a ratio of the molar of the cyclen to the volume of the organic solvent is 1:6 mol/L.

In a preferred embodiment of the present invention, the method (2) preferably comprises the following steps: after the completion of the alkylation reaction, adding an acidic pH value regulator and an organic solvent to adjust the pH value of the reaction system for the complete precipitation of the crude product of DOTA.

In the present invention, the solvent for recrystallization is water or a mixed solvent of water and an organic solvent. Wherein, the organic solvent is a conventional organic solvent which is miscible with water in the art. The organic solvent of the present invention is preferably selected from the group consisting of acetone, acetonitrile, methanol, ethanol, isopropanol, and tetrahydrofuran; further preferably methanol and/or ethanol. When the solvent for recrystallization is a mixed solvent of water and an organic solvent, the volume ratio of the water to the organic solvent can be a conventional ratio in the art; preferably 1:1-1:20; further preferably 1:2-1:15; further more preferably 1:3-1:10; most preferably 1:3-1:5.

In the present invention, the mass/volume ratio of the crude product of DOTA to the solvent for recrystallization can be a conventional ratio for DOTA recrystallization in the art. The amount thereof is usually such that when under heating condition (e.g., solvent reflux temperature), the crude product of DOTA is substantially dissolved or completely dissolved in the solvent, and the resulting mixture is capable of precipitating DOTA after standing or stirring.

In the present invention, the operation of the recrystallization can be carried out according to a conventional operation for recrystallization in the art, and the operation parameters including temperature, stirring speed and the like are not specifically limited. For example, the recrystallization temperature can be room temperature or the solvent reflux temperature. The temperature, stirring speed, and the like in the recrystallization operation are used to make the crude product of DOTA substantially dissolved or completely dissolved in the solvent. In the present invention, when the recrystallization is carried out in industrial production, the skilled in the art understand that a technical mean such as slurrying or heating/cooling step and so on can be used to achieve the same technical effect as the recrystallization.

In the present invention, when the recrystallization is carried out in industrial production, the skilled in the art understand that multiple operations can be performed to make the product more pure.

In the present invention, after completion of the recrystallization, it is preferred to further dry the product obtained by recrystallization to remove the low-boiling point solvents therein, and further preferred to carry out the drying at 60° C.

The preparation method of the present invention can be further applied to the preparation of a salt of 1,4,7,10-tetraazacyclododecane-1,4,7,10-tetraacetic acid (DOTA), or a hydrate thereof, or a series of gadolinium (Gd) of industrial downstream product thereof such as Gadoteric acid, Gadoterate meglumine, Gadobutrol, etc.

The preferred embodiments of the present invention can be obtained by arbitrary combination of the preferred conditions without departing from the common knowledge in the art.

The reagents and starting materials used in the present invention are commercially available.

The positive effects of the present invention are:

1) The present invention can effectively reach the isoelectric point of DOTA by controlling the pH value. Compared with the prior art, the requirement for strong acid resistance of the reaction kettle can be avoided, and the service life of the equipment can be prolonged.

2) In the present invention, the inorganic salt impurities in the product can be removed and a high-quality DOTA product can be obtained by designing the reaction parameters and the purification process parameters, and only simple crystallization purification is required in the synergistic cooperation. Compared with the prior art, the invention does not need to use the respective ion exchange resin and reduces the post-process of concentrating water, and avoids low-temperature freezing, simplifies the equipment requirements and processes, facilitates the industrial scale-up production, and effectively reduces the production cost at the same time.

3) The present invention deeply studies the difference in the solubility data of lithium salts, sodium salts and potassium salts in water and organic solvent, and lithium salt is selected as the acid-binding agent in preferred embodiments, thereby avoiding the complexity in the later purification process of the present invention, and effectively controlling the limits of lithium ions.

4) According to the preparation method of the present invention, the DOTA products obtained by some embodiments of the present invention have a high yield, a purity of more than 99.0%, a single impurity content of ≤0.05%, a burning residue of <0.10%, which conform to the quality standard of the pharmaceutical raw materials of the product.

DETAILED DESCRIPTION OF THE PREFERRED EMBODIMENT

Figure 1:
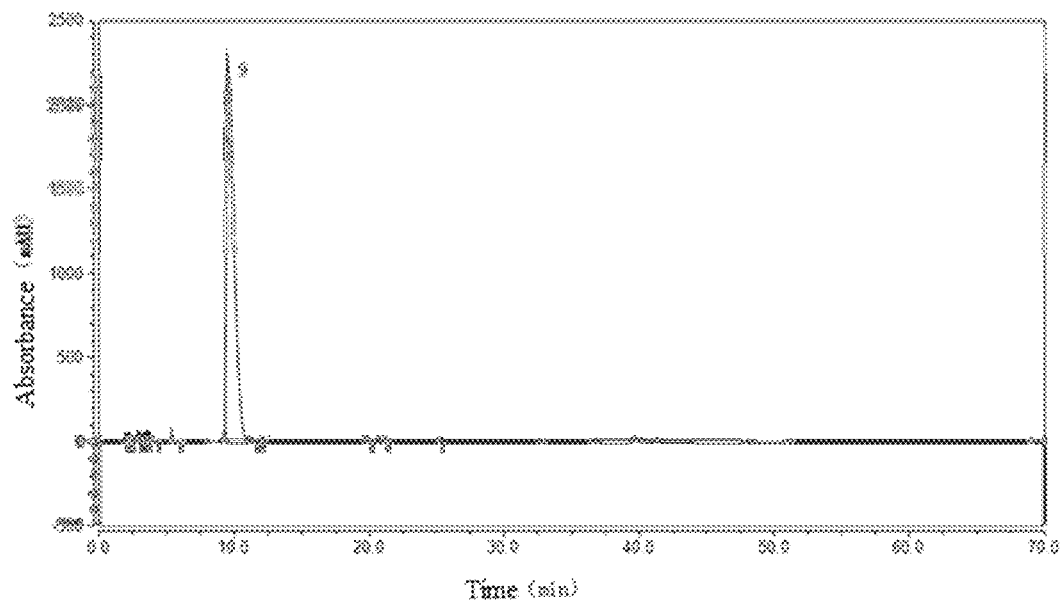
FIG. 1 is the HPLC purity spectra of the product obtained in Embodiment 2.

Unless otherwise specified, in the following embodiments:

Determination Method of the Residue on Ignition:

A porcelain crucible which was ignited for 30 minutes at 600° C.±50° C. and cooled in a desiccator, was accurately weighed ($m_1$), and 1.0 g of test sample was added and accurately weighed ($m_2$). The sample was moistened with 1 mL of sulfuric acid, and then slowly heated at a temperature as low as practicable until the test sample was thoroughly charred, and followed by cooling. The residue was moistened with 1 mL of sulfuric acid, and slowly heated until white fumes were no longer evolved. It was ignited thoroughly to an ash at 600° C.±50° C., cooled in a desiccator, and accurately weighed ($m_3$), followed by calculating the percentage of residue. If the residue content exceeds the limit, repeat the moistening with sulfuric acid, heating, ignition for 30 minutes and accurate weighing ($m_n$), until the weight difference between the two consecutive residues on ignition does not exceed 0.5 mg.

$$\omega_{residue\ on\ ignition} = (m_2 - m_3)m(m_2 - m_1) \times 100\%$$

Wherein, $m_1$ refers to the mass of the porcelain crucible, the unit of which is gram (g); $m_2$ refers to the mass of the porcelain crucible containing the sample before the ignition, the unit of which is gram (g); $m_3$ refers to the mass of the porcelain crucible containing the residue after the ignition, the unit of which is gram (g).

In the following embodiments, unless otherwise specified, the operations in which the temperature are not limited are all carried out at room temperature. 36% hydrochloric acid refers to an aqueous solution of hydrochloric acid having a mass fraction of 36%, and the percentage refers to the percentage of the mass of hydrochloric acid to the total mass of the aqueous solution of hydrochloric acid.

In the following embodiments, the operation of adjusting the pH value for the precipitation of the crude product of DOTA is preferably method (1) or method (2) as follows:

The method (1) comprises the following steps: after the completion of the alkylation reaction, adding an acidic pH value regulator to adjust the pH of the reaction system for the complete precipitation of the crude product of DOTA acid salt; and then dissolving it in water; adding alkaline pH value regulator to adjust the pH value of the reaction system for complete precipitation of the crude product of DOTA; the acidic pH value regulator is used in an amount sufficient to lower the pH value of the reaction system to 1 or even below 0.5, thereby completely converting the product of the alkylation reaction (completely deprotonated DOTA) to the fully protonated DOTA acid salt for the complete precipitation from the reaction system. The alkaline pH value regulator is used in an amount sufficient to adjust the pH value of the reaction system close to the isoelectric point of DOTA (preferably 2.0-4.0, more preferably 3.0-4.0 in the present invention), thereby completely converting the DOTA acid salt to free DOTA for the complete precipitation from its aqueous solution.

The method (2) comprises the following steps: after the completion of the alkylation reaction, adding an acidic pH value regulator to adjust the pH value of the reaction system for the complete precipitation of the crude product of DOTA. The acidic pH value regulator is used in an amount sufficient to adjust the pH of the reaction system close to the isoelectric point of DOTA (in the present invention, preferably 2.0-4.0, more preferably 3.0-4.0), thereby completely converting the product of the alkylation reaction (completely deprotonated DOTA) to free DOTA.

In the following embodiments, the mass/volume ratio of the crude product of DOTA to the solvent for recrystallization can be a conventional ratio for DOTA recrystallization in the art. The amount thereof is usually such that when under heating condition (e.g., solvent reflux temperature), the crude product of DOTA is substantially dissolved or completely dissolved in the solvent, and the resulting mixture is capable of precipitating DOTA after standing or stirring. If necessary, stirring can be performed during the recrystallization process. The temperature, stirring speed, and the like in the recrystallization operation are used to make the crude product of DOTA substantially dissolved or completely dissolved in the solvent.

Embodiment 1

Cyclen (17.27 g, 100 mmol), lithium hydroxide monohydrate (36.92 g, 880 mmol) and water (80 mL) were added into a three-necked flask (1000 mL) at 0-10° C. A solution of bromoacetic acid (61.14 g, 440 mmol) in water (30 mL) was added at 5-15° C. The mixture was warmed to 20-30° C. and reacted for 24 hours. No surplus of the raw material cyclen was detected by TLC. 36% hydrochloric acid (44.6 g, 440 mmol) and ethanol (600 mL) were added to the system for solids precipitation, followed by filtration. The resulting solids were purified by recrystallization with ethanol/water (volume ratio 3:1) and dried at 60° C. to obtain DOTA.

Yield: 85.5%, HPLC: 99.7%, residue on ignition: 0.05%, moisture: 7.80%.

Embodiment 2

Cyclen (17.27 g, 100 mmol), lithium hydroxide monohydrate (36.92 g, 880 mmol) and water (80 mL) were added into a three-necked flask (1000 mL) at 0-10° C. A solution of bromoacetic acid (61.14 g, 440 mmol) in water (30 mL) was added at 5-15° C. The mixture was kept at 5-15° C. and reacted for 24 hours. No surplus of the raw material cyclen was detected by TLC. 36% hydrochloric acid (44.6 g, 440 mmol) and ethanol (600 mL) were added to the system for solids precipitation, followed by filtration. The resulting solids were purified by recrystallization with ethanol/water (volume ratio 3:1) and dried at 60° C. to obtain DOTA.

Yield: 78.0%, HPLC: 99.9%, residue on ignition: 0.05%, moisture: 6.25%.

Wherein, the HPLC spectrum of the product was shown in FIG. 1. The HPLC purity data in FIG. 1 was shown in Table 1, and the retention time of which was 9.447 minute.

TABLE 1

| No. | Retention time (min) | Peak area (mAU*min) | Peak height (mAU) | Relative peak area (%) | Relative peak height (%) |
|---|---|---|---|---|---|
| 1 | 1.987 | 0.400 | 7.694 | 0.03 | 0.33 |
| 2 | 2.213 | 0.021 | 0.230 | 0.00 | 0.01 |
| 3 | 2.357 | 0.057 | 0.553 | 0.00 | 0.02 |
| 4 | 2.983 | 0.020 | 0.137 | 0.00 | 0.01 |
| 5 | 3.297 | 0.426 | 5.453 | 0.03 | 0.23 |
| 6 | 3.707 | 0.052 | 0.443 | 0.00 | 0.02 |
| 7 | 4.027 | 0.280 | 1.288 | 0.02 | 0.06 |
| 8 | 5.710 | 0.113 | 0.473 | 0.01 | 0.02 |
| 9 | 9.447 | 1430.107 | 2307.930 | 99.86 | 99.16 |
| 10 | 12.033 | 0.023 | 0.350 | 0.00 | 0.02 |
| 11 | 19.870 | 0.403 | 2.242 | 0.03 | 0.10 |
| 12 | 21.167 | 0.108 | 0.364 | 0.01 | 0.02 |
| 13 | 25.330 | 0.040 | 0.276 | 0.00 | 0.01 |
| Total | | 1432.052 | 2327.431 | 100.00 | 100.00 |

Embodiment 3

Cyclen (17.27 g, 100 mmol), lithium hydroxide monohydrate (36.92 g, 880 mmol) and water (80 mL) were added into a three-necked flask (1000 mL) at 0-10° C. A solution of bromoacetic acid (61.14 g, 440 mmol) in water (30 mL) was added at 5-15° C. The mixture was heated to 35-45° C. and reacted for 24 hours. No surplus of the raw material cyclen was detected by TLC. 36% hydrochloric acid (44.6 g, 440 mmol) and ethanol (600 mL) were added to the system for solids precipitation, followed by filtration. The resulting solids were purified by recrystallization with ethanol/water (volume ratio 3:1) and dried at 60° C. to obtain DOTA.

Yield: 82.3.0%, HPLC: 99.6%, residue on ignition: 0.06%, moisture: 5.60%.

Embodiment 4

Cyclen (17.27 g, 100 mmol), lithium hydroxide monohydrate (36.92 g, 880 mmol) and water (80 mL) were added into a three-necked flask (1000 mL) at 0-10° C. A solution of bromoacetic acid (61.14 g, 440 mmol) in water (30 mL) was added at 5-15° C. The mixture was heated to 50-60° C. and reacted for 24 hours. No surplus of the raw material cyclen was detected by TLC. 36% hydrochloric acid (44.6 g, 440 mmol) and ethanol (600 mL) were added to the system for solids precipitation, followed by filtration. The resulting solids were purified by recrystallization with ethanol/water (volume ratio 3:1) and dried at 60° C. to obtain DOTA.

Yield: 75.9%, HPLC: 99.7%, residue on ignition: 0.07%, moisture: 6.37%.

Embodiment 5

Cyclen (17.27 g, 100 mmol), lithium hydroxide monohydrate (36.92 g, 880 mmol) and water (80 mL) were added into a three-necked flask (1000 mL) at 0-10° C. A solution of iodoacetic acid (81.82 g, 440 mmol) in water (30 mL) was added at 5-15° C. The mixture was warmed to 20-30° C. and reacted for 24 hours. No surplus of the raw material cyclen was detected by TLC. 36% hydrochloric acid (44.6 g, 440 mmol) and ethanol (600 mL) were added to the system for solids precipitation, followed by filtration. The resulting solids were purified by recrystallization with ethanol/water (volume ratio 3:1) and dried at 60° C. to obtain DOTA.

Yield: 72.0%, HPLC: 99.7%, residue on ignition: 0.02%, moisture: 6.20%.

Embodiment 6

Cyclen (17.27 g, 100 mmol), lithium hydroxide monohydrate (36.92 g, 880 mmol) and water (80 mL) were added into a three-necked flask (1000 mL) at 0-10° C. A solution of choroacetic acid (41.58 g, 440 mmol) in water (30 mL) was added at 5-15° C. The mixture was warmed to 20-30° C. and reacted for 24 hours. No surplus of the raw material cyclen was detected by TLC. 36% hydrochloric acid (44.6 g, 440 mmol) and ethanol (600 mL) were added to the system for solids precipitation, followed by filtration. The resulting solids were purified by recrystallization with ethanol/water (volume ratio 3:1) and dried at 60° C. to obtain DOTA.

Yield: 75.8%, HPLC: 99.8%, residue on ignition: 0.08%, moisture: 7.50%.

Embodiment 7

Cyclen (17.27 g, 100 mmol), lithium hydroxide monohydrate (36.92 g, 880 mmol) and water (80 mL) were added into a three-necked flask (1000 mL) at 0-10° C. A solution of bromoacetic acid (61.14 g, 440 mmol) in water (30 mL) was added at 5-15° C. The mixture was warmed to 20-30° C. and reacted for 24 hours. No surplus of the raw material cyclen was detected by TLC. 40% hydrobromic acid (89.00 g, 440 mmol) and ethanol (600 mL) were added to the system for solids precipitation, followed by filtration. The resulting solids were purified by recrystallization with ethanol/water (volume ratio 3:1) and dried at 60° C. to obtain DOTA.

Yield: 67.8%, HPLC: 99.7%, residue on ignition: 0.02%, moisture: 6.50%.

Embodiment 8

Cyclen (17.27 g, 100 mmol), lithium hydroxide monohydrate (36.92 g, 880 mmol) and water (80 mL) were added into a three-necked flask (1000 mL) at 0-10° C. A solution of bromoacetic acid (61.14 g, 440 mmol) in water (30 mL) was added at 5-15° C. The mixture was warmed to 20-30° C. and reacted for 24 hours. No surplus of the raw material cyclen was detected by TLC. 45% hydroiodic acid (125.07 g, 440 mmol) and ethanol (600 mL) were added to the system for solids precipitation, followed by filtration. The resulting solids were purified by recrystallization with ethanol/water (volume ratio 3:1) and dried at 60° C. to obtain DOTA.

Yield: 77.8%, HPLC: 99.8%, residue on ignition: 0.66%, moisture: 7.40%.

Embodiment 9

Cyclen (17.27 g, 100 mmol), lithium hydroxide monohydrate (36.92 g, 880 mmol) and water (80 mL) were added into a three-necked flask (1000 mL) at 0-10° C. A solution of bromoacetic acid (61.14 g, 440 mmol) in water (30 mL) was added at 5-15° C. The mixture was warmed to 20-30° C. and reacted for 24 hours. No surplus of the raw material cyclen was detected by TLC. 36% hydrochloric acid (44.6 g, 440 mmol) and methanol (600 mL) were added to the system for solids precipitation, followed by filtration. The resulting solids were purified by recrystallization with methanol/water (volume ratio 3:1) and dried at 60° C. to obtain DOTA.

Yield: 18.5%, HPLC: 99.7%, residue on ignition: 0.02%, moisture: 6.20%.

Embodiment 10

Cyclen (17.27 g, 100 mmol), lithium hydroxide monohydrate (36.92 g, 880 mmol) and water (80 mL) were added into a three-necked flask (1000 mL) at 0-10° C. A solution of bromoacetic acid (61.14 g, 440 mmol) in water (30 mL) was added at 5-15° C. The mixture was warmed to 20-30° C. and reacted for 24 hours. No surplus of the raw material cyclen was detected by TLC. 36% hydrochloric acid (44.6 g, 440 mmol) and acetonitrile (600 mL) were added to the system for solids precipitation, followed by filtration. The resulting solids were purified by recrystallization with acetonitrile/water (volume ratio 3:1) and dried at 60° C. to obtain DOTA.

Yield: 67.0%, HPLC: 99.6%, residue on ignition: 0.08%, moisture: 8.50%.

Embodiment 11

Cyclen (17.27 g, 100 mmol), lithium hydroxide monohydrate (36.92 g, 880 mmol) and water (80 mL) were added into a three-necked flask (1000 mL) at 0-10° C. A solution of bromoacetic acid (61.14 g, 440 mmol) in water (30 mL) was added at 5-15° C. The mixture was warmed to 20-30° C. and reacted for 24 hours. No surplus of the raw material cyclen was detected by TLC. 36% hydrochloric acid (44.6 g, 440 mmol) and isopropanol (600 mL) were added to the system for solids precipitation, followed by filtration. The resulting solids were purified by recrystallization with isopropanol/water (volume ratio 3:1) and dried at 60° C. to obtain DOTA.

Yield: 80.0%, HPLC: 99.4%, residue on ignition: 0.12%, moisture: 5.78%.

Embodiment 12

Cyclen (17.27 g, 100 mmol), lithium hydroxide monohydrate (36.92 g, 880 mmol) and water (80 mL) were added into a three-necked flask (1000 mL) at 0-10° C. A solution of bromoacetic acid (61.14 g, 440 mmol) in water (30 mL) was added at 5-15° C. The mixture was warmed to 20-30° C. and reacted for 24 hours. No surplus of the raw material cyclen was detected by TLC. 36% hydrochloric acid (44.6 g, 440 mmol) and acetone (600 mL) were added to the system for solids precipitation, followed by filtration. The resulting solids were purified by recrystallization with acetone/water (volume ratio 3:1) and dried at 60° C. to obtain DOTA.

Yield: 78.9%, HPLC: 99.2%, residue on ignition: 0.09%, moisture: 6.88%.

Embodiment 13

Cyclen (17.27 g, 100 mmol), lithium hydroxide monohydrate (36.92 g, 880 mmol) and water (80 mL) were added into a three-necked flask (1000 mL) at 0-10° C. A solution of bromoacetic acid (61.14 g, 440 mmol) in water (30 mL) was added at 5-15° C. The mixture was warmed to 20-30° C. and reacted for 24 hours. No surplus of the raw material cyclen was detected by TLC. 36% hydrochloric acid (44.6 g, 440 mmol) and tetrahydrofuran (600 mL) were added to the system for solids precipitation, followed by filtration. The resulting solids were purified by recrystallization with tetrahydrofuran/water (volume ratio 3:1) and dried at 60° C. to obtain DOTA.

Yield: 23.0%, HPLC: 99.0%, residue on ignition: 0.02%, moisture: 8.80%.

Embodiment 14

Cyclen (17.27 g, 100 mmol), lithium hydroxide monohydrate (36.92 g, 880 mmol) and water (80 mL) were added into a three-necked flask (1000 mL) at 0-10° C. A solution of bromoacetic acid (61.14 g, 440 mmol) in water (30 mL) was added at 5-15° C. The mixture was warmed to 20-30° C. and reacted for 24 hours. No surplus of the raw material cyclen was detected by TLC. 36% hydrochloric acid (44.6 g, 440 mmol) and ethanol (600 mL) were added to the system for solids precipitation, followed by filtration. The resulting solids were purified by recrystallization with ethanol/water (volume ratio 1:1) and dried at 60° C. to obtain DOTA.

Yield: 65.7%, HPLC: 99.7%, residue on ignition: 0.02%, moisture: 6.45%.

Embodiment 15

Cyclen (17.27 g, 100 mmol), lithium hydroxide monohydrate (36.92 g, 880 mmol) and water (80 mL) were added into a three-necked flask (1000 mL) at 0-10° C. A solution of bromoacetic acid (61.14 g, 440 mmol) in water (30 mL) was added at 5-15° C. The mixture was warmed to 20-30° C. and reacted for 24 hours. No surplus of the raw material cyclen was detected by TLC. 36% hydrochloric acid (44.6 g, 440 mmol) and ethanol (600 mL) were added to the system for solids precipitation, followed by filtration. The resulting solids were purified by recrystallization with water (mass/ volume ratio of the crude product of DOTA to the water was 1:2) and dried at 60° C. to obtain DOTA.

Yield: 40.0%, HPLC: 99.7%, residue on ignition: 0.03%, moisture: 8.80%.

Embodiment 16

Cyclen (17.27 g, 100 mmol), lithium hydroxide monohydrate (36.92 g, 880 mmol) and water (80 mL) were added into a three-necked flask (1000 mL) at 0-10° C. A solution of bromoacetic acid (61.14 g, 440 mmol) in water (30 mL) was added at 5-15° C. The mixture was warmed to 20-30° C. and reacted for 24 hours. No surplus of the raw material cyclen was detected by TLC. 36% hydrochloric acid (44.6 g, 440 mmol) and ethanol (600 mL) were added to the system for solids precipitation, followed by filtration. The resulting solids were purified by recrystallization with water (mass/volume ratio of the crude product of DOTA to the water was 1:1) and dried at 60° C. to obtain DOTA.

Yield: 25.0%, HPLC: 99.7%, residue on ignition: 0.01%, moisture: 7.50%.

Embodiment 17

Cyclen (17.27 g, 100 mmol), lithium hydroxide monohydrate (36.92 g, 880 mmol) and water (80 mL) were added into a three-necked flask (1000 mL) at 0-10° C. A solution of bromoacetic acid (61.14 g, 440 mmol) in water (30 mL) was added at 5-15° C. The mixture was warmed to 20-30° C. and reacted for 24 hours. No surplus of the raw material cyclen was detected by TLC. 36% hydrochloric acid (44.6 g, 440 mmol) and ethanol (600 mL) were added to the system for solids precipitation, followed by filtration. The resulting solids were purified by recrystallization with ethanol/water (volume ratio 5:1) and dried at 60° C. to obtain DOTA.

Yield: 83.4%, HPLC: 99.4%, residue on ignition: 0.09%, moisture: 8.22%.

Embodiment 18

Cyclen (17.27 g, 100 mmol), lithium hydroxide monohydrate (36.92 g, 880 mmol) and water (80 mL) were added into a three-necked flask (1000 mL) at 0-10° C. A solution of bromoacetic acid (61.14 g, 440 mmol) in water (30 mL) was added at 5-15° C. The mixture was warmed to 20-30° C. and reacted for 24 hours. No surplus of the raw material cyclen was detected by TLC. 36% hydrochloric acid (44.6 g, 440 mmol) and ethanol (600 mL) were added to the system for solids precipitation, followed by filtration. The resulting solids were purified by recrystallization with ethanol/water (volume ratio 10:1) and dried at 60° C. to obtain DOTA.

Yield: 85.5%, HPLC: 99.0%, residue on ignition: 0.09%, moisture: 7.81%.

Embodiment 19

Cyclen (17.27 g, 100 mmol), lithium hydroxide monohydrate (36.92 g, 880 mmol) and water (80 mL) were added into a three-necked flask (1000 mL) at 0-10° C. A solution of bromoacetic acid (61.14 g, 440 mmol) in water (30 mL) was added at 5-15° C. The mixture was warmed to 20-30° C. and reacted for 24 hours. No surplus of the raw material cyclen was detected by TLC. 36% hydrochloric acid (44.6 g, 440 mmol) and ethanol (600 mL) were added to the system for solids precipitation, followed by filtration. The resulting solids were purified by recrystallization with ethanol/water (volume ratio 15:1) and dried at 60° C. to obtain DOTA.

Yield: 87.8%, HPLC: 99.0%, residue on ignition: 0.119%, moisture: 7.90%.

Embodiment 20

Cyclen (17.27 g, 100 mmol), lithium hydroxide monohydrate (36.92 g, 880 mmol) and water (80 mL) were added into a three-necked flask (1000 mL) at 0-10° C. A solution of bromoacetic acid (61.14 g, 440 mmol) in water (30 mL) was added at 5-15° C. The mixture was warmed to 20-30° C. and reacted for 24 hours. No surplus of the raw material cyclen was detected by TLC. 36% hydrochloric acid (44.6 g, 440 mmol) and ethanol (600 mL) were added to the system for solids precipitation, followed by filtration. The resulting solids were purified by recrystallization with ethanol/water (volume ratio 20:1) and dried at 60° C. to obtain DOTA.

Yield: 87.0%, HPLC: 99.1%, residue on ignition: 0.09%, moisture: 6.78%.

Embodiment 21

Cyclen (17.27 g, 100 mmol), lithium hydroxide monohydrate (35.25 g, 840 mmol) and water (80 mL) were added into a three-necked flask (1000 mL) at 0-10° C. A solution of bromoacetic acid (61.14 g, 440 mmol) in water (30 mL) was added at 5-15° C. The mixture was warmed to 20-30° C. and reacted for 24 hours. No surplus of the raw material cyclen was detected by TLC. 36% hydrochloric acid (42.6 g, 420 mmol) and ethanol (600 mL) were added to the system for solids precipitation, followed by filtration. The resulting solids were purified by recrystallization with ethanol/water (volume ratio 3:1) and dried at 60° C. to obtain DOTA.

Yield: 81.3%, HPLC: 99.7%, residue on ignition: 0.02%, moisture: 6.92%.

Embodiment 22

Cyclen (17.27 g, 100 mmol), lithium hydroxide monohydrate (38.60 g, 920 mmol) and water (80 mL) were added into a three-necked flask (1000 mL) at 0-10° C. A solution of bromoacetic acid (63.93 g, 460 mmol) in water (30 mL) was added at 5-15° C. The mixture was warmed to 20-30° C. and reacted for 24 hours. No surplus of the raw material cyclen was detected by TLC. 36% hydrochloric acid (46.64 g, 460 mmol) and ethanol (600 mL) were added to the system for solids precipitation, followed by filtration. The resulting solids were purified by recrystallization with ethanol/water (volume ratio 3:1) and dried at 60° C. to obtain DOTA.

Yield: 78.9%, HPLC: 99.7%, residue on ignition: 0.05%, moisture: 7.20%.

Embodiment 23

Cyclen (17.27 g, 100 mmol), lithium hydroxide monohydrate (40.28 g, 960 mmol) and water (80 mL) were added into a three-necked flask (1000 mL) at 0-10° C. A solution of bromoacetic acid (66.70 g, 480 mmol) in water (30 mL) was added at 5-15° C. The mixture was warmed to 20-30° C. and reacted for 24 hours. No surplus of the raw material cyclen was detected by TLC. 36% hydrochloric acid (48.67 g, 480 mmol) and ethanol (600 mL) were added to the system for solids precipitation, followed by filtration. The resulting solids were purified by recrystallization with ethanol/water (volume ratio 3:1) and dried at 60° C. to obtain DOTA.

Yield: 82.3%, HPLC: 99.7%, residue on ignition: 0.06%, moisture: 7.58%.

Embodiment 24

Cyclen (17.27 g, 100 mmol), lithium hydroxide monohydrate (38.60 g, 920 mmol) and water (80 mL) were added into a three-necked flask (1000 mL) at 0-10° C. A solution of bromoacetic acid (63.93 g, 460 mmol) in water (30 mL) was added at 5-15° C. The mixture was warmed to 20-30° C. and reacted for 24 hours. No surplus of the raw material cyclen was detected by TLC. 36% hydrochloric acid was added to the system to adjust the pH value to 3.4-3.6, and ethanol (600 mL) was added for solids precipitation, followed by filtration. The resulting solids were purified by recrystallization with ethanol/water (volume ratio 3:1) and dried at 60° C. to obtain DOTA.

Yield: 83.0%, HPLC: 99.6%, residue on ignition: 0.05%, moisture: 7.80%.

Embodiment 25

Cyclen (690.0 g, 4 mol), lithium hydroxide monohydrate (1477.2 g, 35.2 mol) and water (1400 mL) were added into a four-necked flask (20 L) at 0-10° C. A solution of bromoacetic acid (2445.6 g, 17.6 mol) in water (1200 mL) was added at 5-15° C. The mixture was warmed to 20-30° C. and reacted for 24 hours. No surplus of the raw material cyclen was detected by TLC. 36% hydrochloric acid (1785.0 g, 17.6 mol) and ethanol (12 L) were added to the system for solids precipitation, followed by filtration. The resulting solids were purified by recrystallization with ethanol/water (volume ratio 3:1) and dried at 60° C. to obtain 1343.0 g of DOTA.

Yield: 83.0%, HPLC: 99.6%, residue on ignition: 0.07%, moisture: 4.92%.

Embodiment 26

Cyclen (6.90 kg, 40.0 mol), lithium hydroxide monohydrate (14.78 kg, 352.0 mol) and water (23.0 kg) were added into a glass-lined reactor (200 L) at 0-10° C. A solution of bromoacetic acid (24.46 kg, 176.0 mol) in water (10 kg) was added at 5-15° C. The mixture was warmed to 20-30° C. and reacted for 24 hours. No surplus of the raw material cyclen was detected by TLC. 36% hydrochloric acid (17.36 kg, 176.0 mol) and ethanol (120 kg) were added to the system for solids precipitation, followed by centrifugation. The resulting solids were purified by recrystallization with ethanol/water (volume ratio 3:1) and dried at 60° C. for 36 hours to obtain 12.95 kg of DOTA.

Yield: 80.1%, HPLC: 99.7%, residue on ignition: 0.05%, moisture: 4.73%.

Embodiment 27

Cyclen (69.0 kg, 400.0 mol), lithium hydroxide monohydrate (147.8 kg, 3523.8 mol) and water (230.0 kg) were added into a glass-lined reactor (2000 L) at 0-10° C. A solution of bromoacetic acid (244.6 kg, 1760.0 mol) in water (100 kg) was added at 5-15° C. The mixture was warmed to 20-30° C. and reacted for 24 hours. No surplus of the raw material cyclen was detected by TLC. 36% hydrochloric acid (173.6 kg, 1760.0 mol) and ethanol (1200 kg) were added to the system for solids precipitation, followed by centrifugation. The resulting solids were purified by recrystallization with ethanol/water (volume ratio 3:1) and dried at 60° C. for 48 hours to obtain 138.5 kg of DOTA.

Yield: 85.6%, HPLC: 99.8%, residue on ignition: 0.04%, moisture: 5.50%.

Embodiment 28

Cyclen (17.27 g, 100 mmol), sodium hydroxide (35.20 g, 880 mmol) and water (80 mL) were added into a three-necked flask (1000 mL) at 0-10° C. A solution of bromoacetic acid (61.14 g, 440 mmol) in water (30 mL) was added at 5-15° C. The mixture was warmed to 20-30° C. and reacted for 24 hours. No surplus of the raw material cyclen was detected by TLC. 36% hydrochloric acid (44.6 g, 440 mmol) and ethanol (600 mL) were added to the system for solids precipitation, followed by filtration. The resulting solids were purified by recrystallization with ethanol/water (volume ratio 3:1) and dried at 60° C. to obtain DOTA.

Yield: 90.5%, HPLC: 57.5%, residue on ignition: 20.8%, moisture: 8.55%.

Embodiment 29

Cyclen (17.27 g, 100 mmol), potassium hydroxide (49.28 g, 880 mmol) and water (80 mL) were added into a three-necked flask (1000 mL) at 0-10° C. A solution of bromoacetic acid (61.14 g, 440 mmol) in water (30 mL) was added at 5-15° C. The mixture was warmed to 20-30° C. and reacted for 24 hours. No surplus of the raw material cyclen was detected by TLC. 36% hydrochloric acid (44.6 g, 440 mmol) and ethanol (600 mL) were added to the system for solids precipitation, followed by filtration. The resulting solids were purified by recrystallization with ethanol/water (volume ratio 3:1) and dried at 60° C. to obtain DOTA.

Yield: 88.0%, HPLC: 47.5%, residue on ignition: 21.3%, moisture: 7.23%.

Embodiment 30

Cyclen (17.27 g, 100 mmol), sodium acetate (72.16 g, 880 mmol) and water (80 mL) were added into a three-necked flask (1000 mL) at 0-10° C. A solution of bromoacetic acid (61.14 g, 440 mmol) in water (30 mL) was added at 5-15° C. The mixture was warmed to 20-30° C. and reacted for 24 hours. No surplus of the raw material cyclen was detected by TLC. 36% hydrochloric acid (44.6 g, 440 mmol) and ethanol (600 mL) were added to the system for solids precipitation, followed by filtration. The resulting solids were purified by recrystallization with ethanol/water (volume ratio 3:1) and dried at 60° C. to obtain DOTA.

Yield: 86.7%, HPLC: 78.5%, residue on ignition: 24.8%, moisture: 8.80%.

Embodiment 31

Cyclen (17.27 g, 100 mmol), lithium hydroxide monohydrate (36.92 g, 880 mmol) and water (80 mL) were added into a three-necked flask (1000 mL) at 0-10° C. A solution of sodium chloroacetate (51.25 g, 440 mmol) in water (30 mL) was added at 5-15° C. The mixture was warmed to 20-30° C. and reacted for 24 hours. No surplus of the raw material cyclen was detected by TLC. 36% hydrochloric acid (44.6 g, 440 mmol) and ethanol (600 mL) were added to the system for solids precipitation, followed by filtration.

The resulting solids were purified by recrystallization with ethanol/water (volume ratio 3:1) and dried at 60° C. to obtain DOTA.

Yield: 85.0%, HPLC: 89%, residue on ignition: 12.5%, moisture: 7.23%.

Embodiment 32

Cyclen (17.27 g, 100 mmol), sodium hydroxide (35.20 g, 880 mmol) and water (80 mL) were added into a three-necked flask (1000 mL) at 0-10° C. A solution of bromoacetic acid (61.14 g, 440 mmol) in water (30 mL) was added at 5-15° C. The mixture was warmed to 20-30° C. and reacted for 24 hours. No surplus of the raw material cyclen was detected by TLC. 40% hydrobromic acid (89.00 g, 440 mmol) and ethanol (600 mL) were added to the system for solids precipitation, followed by filtration. The resulting solids were purified by recrystallization with ethanol/water (volume ratio 3:1) and dried at 60° C. to obtain DOTA.

Yield: 62.3%, HPLC: 96.8%, residue on ignition: 7.00%, moisture: 8.58%.

Embodiment 33

Cyclen (17.27 g, 100 mmol), sodium hydroxide (35.20 g, 880 mmol) and water (80 mL) were added into a three-necked flask (1000 mL) at 0-10° C. A solution of bromoacetic acid (61.14 g, 440 mmol) in water (30 mL) was added at 5-15° C. The mixture was warmed to 20-30° C. and reacted for 24 hours. No surplus of the raw material cyclen was detected by TLC. 45% hydroiodic acid (125.07 g, 440 mmol) and ethanol (600 mL) were added to the system for solids precipitation, followed by filtration. The resulting solids were purified by recrystallization with ethanol/water (volume ratio 3:1) and dried at 60° C. to obtain DOTA.

Yield: 75.3%, HPLC: 97.8%, residue on ignition: 4.61%, moisture: 8.20%.

Embodiment 34

Cyclen (17.27 g, 100 mmol), sodium hydroxide (35.20 g, 880 mmol) and water (80 mL) were added into a three-necked flask (1000 mL) at 0-10° C. A solution of bromoacetic acid (63.93 g, 460 mmol) in water (30 mL) was added at 5-15° C. The mixture was warmed to 20-30° C. and reacted for 24 hours. No surplus of the raw material cyclen was detected by TLC. 36% hydrochloric acid was added to the system to adjust the pH value of the system <0.5, and cooled to about 0° C. to obtain the solids, followed by filtration. The resulting solids were purified by slurrying with concentrated hydrochloric acid (about 30 mL) to obtain 40.05 g of crude product of DOTA hydrochloride, the HPLC purity of which is 75%. After the resulting crude product was dissolved in another 1 L four-necked flask with water (150 mL), the pH value of the system was adjusted to 3.5-4.0 with triethylamine. Acetone (300 mL) was added thereto with stirring, followed by filtration, and dried at 60° C. to obtain DOTA.

Yield: 90.0%, HPLC: 93.74%, residue on ignition: 7.63%, moisture: 8.80%.

Embodiment 35

Cyclen (17.27 g, 100 mmol), sodium hydroxide (35.20 g, 880 mmol) and water (80 mL) were added into a three-necked flask (1000 mL) at 0-10° C. A solution of bromoacetic acid (63.93 g, 460 mmol) in water (30 mL) was added at 5-15° C. The mixture was warmed to 20-30° C. and reacted for 24 hours. No surplus of the raw material cyclen was detected by TLC. 36% hydrochloric acid was added to the system to adjust the pH value of the system <0.5, and cooled to about 0° C. to obtain the solids, followed by filtration. The resulting solids were purified by slurrying with concentrated hydrochloric acid (30 mL) to obtain 42.00 g of crude product of DOTA hydrochloride, the HPLC purity of which is 75%. After the resulting crude product was dissolved in another 1 L four-necked flask with water (150 mL), the pH value of the system was adjusted to 3.5-4.0 with ammonium hydroxide. Ethanol (300 mL) was added thereto with stirring, followed by filtration, and dried at 60° C. to obtain DOTA.

Yield: 91.3%, HPLC: 89.56%, residue on ignition: 6.60%, moisture: 7.80%.

Embodiment 36

Cyclen (17.27 g, 100 mmol), sodium hydroxide (35.20 g, 880 mmol) and water (80 mL) were added into a three-necked flask (1000 mL) at 0-10° C. A solution of bromoacetic acid (63.93 g, 460 mmol) in water (30 mL) was added at 5-15° C. The mixture was warmed to 20-30° C. and reacted for 24 hours. No surplus of the raw material cyclen was detected by TLC. 36% hydrochloric acid was added to the system to adjust the pH value of the system <0.5, and cooled to about 0° C. to obtain the solids, followed by filtration. The resulting solids were purified by slurrying with concentrated hydrochloric acid (30 mL) to obtain 42.00 g of crude product of DOTA hydrochloride, the HPLC purity of which is 75%. After the resulting crude product was dissolved in another 1 L four-necked flask with water (150 mL), the pH value of the system was adjusted to 3.5-4.0 with ammonium hydroxide. Acetone (300 mL) was added thereto with stirring, followed by filtration, and dried at 60° C. to obtain DOTA.

Yield: 88.6%, HPLC: 92.6%, residue on ignition: 7.58%, moisture: 6.08%.

Embodiment 37

Cyclen (17.27 g, 100 mmol), sodium hydroxide (35.20 g, 880 mmol) and water (80 mL) were added into a three-necked flask (1000 mL) at 0-10° C. A solution of bromoacetic acid (63.93 g, 460 mmol) in water (30 mL) was added at 5-15° C. The mixture was warmed to 20-30° C. and reacted for 24 hours. No surplus of the raw material cyclen was detected by TLC. 36% hydrochloric acid was added to the system to adjust the pH value of the system <0.5, and cooled to about 0° C. to obtain the solids, followed by filtration. The resulting solids were purified by slurrying with concentrated hydrochloric acid (30 mL) to obtain 40.05 g of crude product of DOTA hydrochloride, the HPLC purity of which is 75%. After the resulting crude product was dissolved in another 1 L four-necked flask with water (150 mL), the pH value of the system was adjusted to 3.5-4.0 with triethylamine. Ethanol (300 mL) was added thereto with stirring, followed by filtration, and dried at 60° C. to obtain DOTA.

Yield: 88.8%, HPLC: 93.3%, residue on ignition: 5.68%, moisture: 8.50%.

Embodiment 38

Cyclen (17.27 g, 100 mmol), lithium hydroxide monohydrate (18.46 g, 440 mmol) and water (80 mL) were added into a three-necked flask (1000 mL) at 0-10° C. A solution of sodium bromoacetate (51.25 g, 440 mmol) in water (30 mL) was added at 5-15° C. The mixture was warmed to 20-30° C. and reacted for 24 hours. No surplus of the raw material cyclen was detected by TLC. 36% hydrochloric acid (44.6 g, 880 mmol) and ethanol (600 mL) were added to the system for solids precipitation, followed by filtration. The resulting solids were purified by recrystallization with ethanol/water (volume ratio 3:1) and dried at 60° C. to obtain DOTA.

Yield: 67.8%, HPLC: 75.5%, residue on ignition: 1.23%, moisture: 7.23%.

Figure 2:
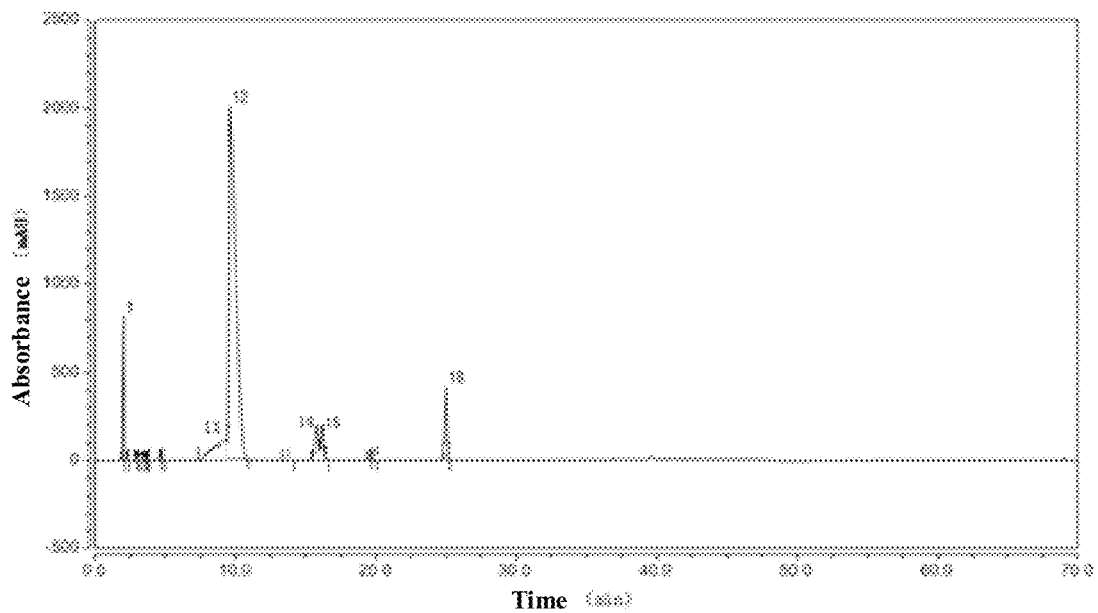
FIG. 2 is the HPLC purity spectra of the product obtained in Embodiment 38.

Wherein, the HPLC spectrum of the product was shown in FIG. 2, and the purity data was shown in Table 2; the retention time of which was 9.580 minute.

TABLE 2

| No. | Retention time (min) | Peak area (mAU*min) | Peak height (mAU) | Relative peak area (%) | Relative peak height (%) |
|---|---|---|---|---|---|
| 1 | 2.013 | 46.548 | 820.378 | 3.21 | 21.20 |
| 2 | 2.363 | 0.202 | 3.863 | 0.01 | 0.10 |
| 3 | 2.937 | 0.482 | 7.992 | 0.03 | 0.21 |
| 4 | 3.090 | 0.087 | 1.183 | 0.01 | 0.03 |
| 5 | 3.383 | 0.380 | 6.140 | 0.03 | 0.16 |
| 6 | 3.600 | 0.129 | 1.852 | 0.01 | 0.05 |
| 7 | 3.690 | 0.174 | 4.132 | 0.01 | 0.11 |
| 8 | 3.823 | 0.371 | 10.385 | 0.03 | 0.27 |
| 9 | 4.670 | 0.316 | 3.844 | 0.02 | 0.10 |
| 10 | 4.853 | 0.715 | 6.470 | 0.05 | 0.17 |
| 11 | 9.200 | 124.679 | 123.442 | 8.61 | 3.19 |
| 12 | 9.580 | 1093.166 | 2009.557 | 75.47 | 51.92 |
| 13 | 13.763 | 0.970 | 3.447 | 0.07 | 0.09 |
| 14 | 15.797 | 56.041 | 210.015 | 3.87 | 5.43 |
| 15 | 16.200 | 49.218 | 225.607 | 3.40 | 5.83 |
| 16 | 19.600 | 1.151 | 5.978 | 0.08 | 0.15 |
| 17 | 19.817 | 1.841 | 9.535 | 0.13 | 0.25 |
| 18 | 24.983 | 72.020 | 416.489 | 4.97 | 10.76 |
| Total | | 1448.488 | 3870.310 | 100.00 | 100.00 |

Embodiment 39

Cyclen (17.27 g, 100 mmol), lithium hydroxide monohydrate (18.46 g, 440 mmol) and water (80 mL) were added into a three-necked flask (1000 mL) at 0-10° C. A solution of lithium chloroacetate (44.19 g, 440 mmol) in water (30 mL) was added at 5-15° C. The mixture was warmed to 20-30° C. and reacted for 24 hours. No surplus of the raw material cyclen was detected by TLC. 36% hydrochloric acid (44.6 g, 880 mmol) and ethanol (600 mL) were added to the system for solids precipitation, followed by filtration. The resulting solids were purified by recrystallization with ethanol/water (volume ratio 3:1) and dried at 60° C. to obtain DOTA.

Yield: 43.8%, HPLC: 99.6%, residue on ignition: 0.07%, moisture: 6.50%.

Embodiment 40

Cyclen (17.27 g, 100 mmol), lithium hydroxide monohydrate (18.46 g, 440 mmol) and water (80 mL) were added into a three-necked flask (1000 mL) at 0-10° C. A solution of potassium iodoacetate (98.58 g, 440 mmol) in water (30 mL) was added at 5-15° C. The mixture was warmed to 20-30° C. and reacted for 24 hours. No surplus of the raw material cyclen was detected by TLC. 36% hydrochloric acid (44.6 g, 880 mmol) and ethanol (600 mL) were added to the system for solids precipitation, followed by filtration. The resulting solids were purified by recrystallization with ethanol/water (volume ratio 3:1) and dried at 60° C. to obtain DOTA.

Yield: 62.5%, HPLC: 86.0%, residue on ignition: 12.30%, moisture: 6.50%.

Embodiment 41

Cyclen (17.27 g, 100 mmol), lithium hydroxide monohydrate (18.46 g, 440 mmol) and water (80 mL) were added into a three-necked flask (1000 mL) at 0-10° C. A solution of sodium iodoacetate (91.49 g, 440 mmol) in water (30 mL) was added at 5-15° C. The mixture was warmed to 20-30° C. and reacted for 24 hours. No surplus of the raw material cyclen was detected by TLC. 36% hydrochloric acid (44.6 g, 880 mmol) and ethanol (600 mL) were added to the system for solids precipitation, followed by filtration. The resulting solids were purified by recrystallization with ethanol/water (volume ratio 3:1) and dried at 60° C. to obtain DOTA.

Yield: 51.8%, HPLC: 87.0%, residue on ignition: 11.80%, moisture: 7.90%.

Embodiment 42

Cyclen (17.27 g, 100 mmol), lithium hydroxide monohydrate (36.92 g, 880 mmol) and water (80 mL) were added into a three-necked flask (1000 mL) at 0-10° C. A solution of ethyl bromoacetate (73.48 g, 440 mmol) in water (30 mL) was added at 5-15° C. The mixture was warmed to 20-30° C. and reacted for 24 hours. No surplus of the raw material cyclen was detected by TLC. 36% hydrochloric acid (44.6 g, 880 mmol) and ethanol (600 mL) were added to the system for solids precipitation, followed by filtration. The resulting solids were purified by recrystallization with ethanol/water (volume ratio 3:1) and dried at 60° C. to obtain DOTA.

Yield: 24.8%, HPLC: 98.5%, residue on ignition: 0.25%, moisture: 8.80%.

Embodiment 43

Cyclen (17.27 g, 100 mmol), lithium hydroxide monohydrate (36.92 g, 880 mmol) and water (80 mL) were added into a three-necked flask (1000 mL) at 0-10° C. A solution of methyl chloroacetate (47.75 g, 440 mmol) in water (30 mL) was added at 5-15° C. The mixture was warmed to 20-30° C. and reacted for 24 hours. No surplus of the raw material cyclen was detected by TLC. 36% hydrochloric acid (44.6 g, 880 mmol) and ethanol (600 mL) were added to the system for solids precipitation, followed by filtration. The resulting solids were purified by recrystallization with ethanol/water (volume ratio 3:1) and dried at 60° C. to obtain DOTA.

Yield: 32.5%, HPLC: 98.7%, residue on ignition: 0.18%, moisture: 5.28%.

Embodiment 44

Cyclen (40.00 g), sodium hydroxide (81.80 g) and water (162 mL) were added into a four-necked flask (500 mL) at 15-25° C. A solution of bromoacetic acid (142 g) in water (50 mL) was added at 15-25° C. The mixture was heated to 60° C. and reacted with stirring until no surplus of the raw material cyclen was detected by TLC. Concentrated hydrochloric acid (210 mL) was added to the system to adjust the pH value <0.5, and cooled to about 0° C. to obtain the solids, followed by filtration. The resulting solids were purified by recrystallization with concentrated hydrochloric acid (120 mL) to obtain 119.6 g of crude product of DOTA hydrochloride, the HPLC purity of which is 75%. After the resulting crude product was dissolved in another 1 L four-necked flask with water (500 mL), the pH value of the system was adjusted to 3-4 with triethylamine (about 50 mL). Acetone (1 L) was added thereto with stirring, followed by filtration, and dried to obtain DOTA.

Yield: 90%, HPLC: 93.74%, residue on ignition: 7.63%, moisture:

Comparative Embodiment 1 (Referred to WO2013076743)

Cyclen (17.27 g, 100 mmol), sodium hydroxide (35.20 g, 880 mmol) and water (170 mL) were added into a three-necked flask (1000 mL) at 0-10° C. A solution of bromoacetic acid (63.93 g, 460 mmol) in water (30 mL) was added at 0-10° C., followed by addition of sodium hydroxide to maintain the pH value of the system at 10-10.5. The mixture was heated to 70-75° C. and reacted for 24 hours. No surplus of the raw material cyclen was detected by TLC. 36% Hydroiodic acid was added to the system to adjust the pH value of the system <0.75, and cooled to about 0° C. to obtain the solids, followed by filtration. The resulting solids were slurried and recrystallized with water until the residue on ignition in the DOTA hydrochloride was <0.10%. After the resulting crude product was dissolved in another 500 L four-necked flask with water (80 mL), the pH value of the system was adjusted to 2.5-3.0 by A26 OH ion exchange resin, followed by filtration. The filtrate was concentrated to 20-30 mL. Acetone (180 mL) was added thereto for solids precipitation, followed by filtration, and dried at 60° C. to obtain DOTA.

Yield: 72.3%, HPLC: 99.3%, residue on ignition: 0.04%, moisture: 4.60%.

Comparative Embodiment 2

Cyclen (17.27 g, 100 mmol), sodium hydroxide (35.20 g, 880 mmol) and water (170 mL) were added into a three-necked flask (1000 mL) at 0-10° C. A solution of bromoacetic acid (63.93 g, 460 mmol) in water (30 mL) was added at 0-10° C., followed by addition of sodium hydroxide to maintain the pH value of the system at 10-10.5. The mixture was heated to 70-75° C. and reacted for 24 hours. No surplus of the raw material cyclen was detected by TLC. 36% Hydroiodic acid was added to the system to adjust the pH value of the system <0.75, and cooled to about 0° C. to obtain the solids, followed by filtration. The resulting solids were slurried and recrystallized with water until the residue on ignition in the DOTA hydrochloride was <0.10%. After the resulting crude product was dissolved in another 500 L four-necked flask with water (80 mL), the pH value of the system was adjusted to 2.5-3.0 with ammonium hydroxide, followed by filtration. The filtrate was concentrated to 20-30 mL. Acetone (180 mL) was added thereto for solids precipitation, followed by filtration, and dried at 60° C. to obtain DOTA.

Yield: 60.3%, HPLC: 99.2%, residue on ignition: 0.04%, moisture: 5.80%.

Comparative Embodiment 3

Cyclen (17.27 g, 100 mmol), sodium hydroxide (35.20 g, 880 mmol) and water (170 mL) were added into a three-necked flask (1000 mL) at 0-10° C. A solution of bromoacetic acid (63.93 g, 460 mmol) in water (30 mL) was added at 0-10° C., followed by addition of sodium hydroxide to maintain the pH value of the system at 10-10.5. The mixture was heated to 70-75° C. and reacted for 24 hours. No surplus of the raw material cyclen was detected by TLC. 36% Hydroiodic acid (44.6 g, 440 mmol) and ethanol were added to the system for solids precipitation, followed by filtration. The resulting solids were recrystallized with ethanol/water (volume ratio 3:1).

Yield: 78.0%, HPLC: 88.0%, residue on ignition: 13.50%, moisture: 7.80%.

Although the specific embodiments of the present invention are described above, those skilled in the art should understand that these are only for exemplary illustration, and various modifications and changes can be made without departing from the broader scope of the present invention. Accordingly, the scope of the present invention is defined by the appended claims.

What is claimed is:
1. A method for preparing DOTA,
comprising the following steps: carrying out an alkylation reaction on cyclen and XCH$_2$COOR in the presence of an acid-binding agent in water;
adjusting a pH value to precipitate a crude product of DOTA; and
recrystallizing;
wherein R is H, lithium or C$_1$-C$_4$ alkyl;
X is chlorine, bromine or iodine,
a solvent for recrystallization is water or a mixed solvent of water and an organic solvent;
the acid-binding agent is lithium hydroxide monohydrate;

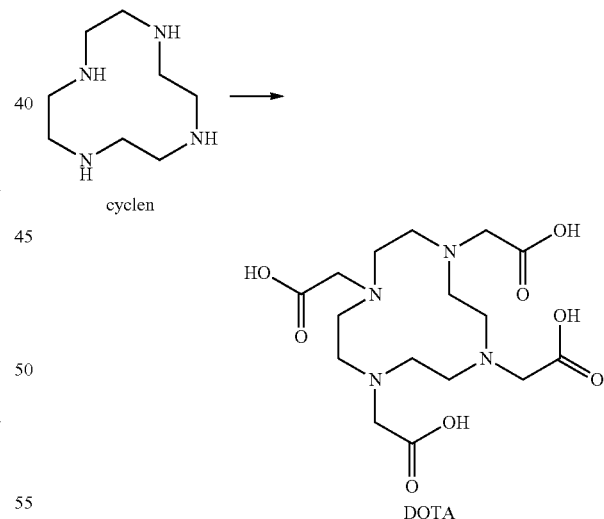

2. The method of claim 1, wherein,
a molar ratio of the acid-binding agent to the cyclen is 8.0:1 to 10.0:1;
and/or, a molar ratio of the XCH$_2$COOR to the cyclen is 4.0:1 to 5.0:1;
and/or, the XCH$_2$COOR is formulated into an aqueous solution thereof, and then added to the above reaction system;
and/or, a molar concentration of the cyclen in the reaction system is 0.5 to 1.5 mol/L.

3. The method of claim 2, wherein,
the molar ratio of the acid-binding agent to the cyclen is 8.4:1 to 9.2:1;
and/or, when R is a $C_1$-$C_4$ alkyl, then the $C_1$-$C_4$ alkyl is methyl, ethyl, n-propyl, isopropyl, n-butyl, isobutyl or tert-butyl;
and/or, the molar ratio of the $XCH_2COOR$ to the cyclen is 4.2:1 to 4.6:1;
and/or, the $XCH_2COOR$ is formulated into an aqueous solution thereof, and then added to the above reaction system; an aqueous solution having a molar concentration of 12.0-18.0 mol/L;
and/or, the molar concentration of the cyclen in the reaction system is 0.9 to 1.0 mol/L.

4. The method of claim 1, wherein,
the $XCH_2COOR$ is selected from the group consisting of chloroacetic acid, and bromoacetic acid.

5. The method of claim 1, wherein,
the $XCH_2COOR$ is bromoacetic acid.

6. The method of claim 1, wherein,
a reaction temperature of the alkylation reaction is −10° C. to 60° C.

7. The method of claim 6, wherein,
the reaction temperature of the alkylation reaction is 5-50° C.;
and/or, the addition order of the reactants for the alkylation reaction is: adding the cyclen, the acid-binding agent and the water at 0-10° C.; then adding the $XCH_2COOR$ or an aqueous solution thereof at 5-15° C.

8. The method of claim 1, wherein, the operation of adjusting the pH value for the precipitation of the crude product of DOTA is method (1) or method (2) as follows:
the method (1) comprises the following steps: after the completion of the alkylation reaction, adding an acidic pH value regulator to adjust the pH of the reaction system for the complete precipitation of the crude product of DOTA acid salt; and then dissolving it in water; adding alkaline pH value regulator to adjust the pH value of the reaction system for complete precipitation of the crude product of DOTA;
the method (2) comprises the following steps: after the completion of the alkylation reaction, adding an acidic pH value regulator to adjust the pH value of the reaction system for the complete precipitation of the crude product of DOTA.

9. The method of claim 8, wherein,
in the method (1), the acidic pH value regulator is selected from the group consisting of hydrochloric acid, hydrobromic acid, hydroiodic acid, nitric acid and sulfuric acid;
and/or, in the method (1), the acidic pH value regulator is used in an amount sufficient to lower the pH of the reaction system below 1;
and/or, in the method (1), the alkaline pH value regulator is selected from the group consisting of ammonia hydroxide, triethylamine and triisopropylamine;
and/or, in the method (1), the alkaline pH value regulator is used in an amount sufficient to adjust the pH value of the reaction system to 2.0-4.0;
and/or, in the method (2), the acidic pH value regulator is selected from the group consisting of hydrochloric acid, hydrobromic acid, hydroiodic acid, nitric acid and sulfuric acid;
and/or, in the method (2), the acidic pH value regulator is used in an amount sufficient to adjust the pH value of the reaction system to 2.0-4.0;
and/or, in the method (2), a molar concentration ratio of the hydrogen proton in the acidic pH value regulator to the cyclen is 4.4:1, or a molar concentration ratio of the hydrogen proton in the acidic pH value regulator to the acid-binding agent is 1:2;
and/or, in the method (2), the organic solvent is selected from methanol, ethanol, isopropanol, tetrahydrofuran, acetone and acetonitrile;
and/or, in the method (2), a ratio of the molar amount of the cyclen to the volume of the organic solvent is 1:6 mol/L.

10. The method of claim 9, wherein,
in the method (1), the acidic pH value regulator is 36% w/w aqueous hydrochloric acid solution;
and/or, in the method (1), the acidic pH value regulator is used in an amount sufficient to lower the pH value of the reaction system below 0.5;
and/or, in the method (1), the alkaline pH value regulator is triethylamine;
and/or, in the method (1), the alkaline pH value regulator is used in an amount sufficient to adjust the pH value of the reaction system to 3.0-4.0;
and/or, in the method (2), the acidic pH value regulator is 36% w/w aqueous hydrochloric acid solution;
and/or, in the method (2), the acidic pH value regulator is used in an amount sufficient to adjust the pH value of the reaction system to 3.0-4.0;
and/or, in the method (2), the organic solvent is selected from methanol and/or ethanol.

11. The method of claim 1, wherein,
when the solvent for recrystallization is a mixed solvent of water and an organic solvent, then the organic solvent is selected from the group consisting of acetone, acetonitrile, methanol, ethanol, isopropanol, and tetrahydrofuran;
and/or, in the recrystallization, the volume ratio of the water to the organic solvent is 1:1 to 1:20.

12. The method of claim 11, wherein,
when the solvent for recrystallization is a mixed solvent of water and an organic solvent, then the organic solvent is methanol and/or ethanol;
and/or, in the recrystallization, the volume ratio of the water to the organic solvent is 1:2 to 1.15.

13. The method of claim 12, wherein, in the recrystallization, the volume ratio of the water to the organic solvent is 1:3 to 1:10.

14. The method of claim 13, wherein, in the recrystallization, the volume ratio of the water to the organic solvent is 1:3 to 1:5.

15. The method of claim 1, wherein, after the completion of the recrystallization, further comprising an operation of: drying the resulting product to remove the low-boiling point solvents.

16. The method of claim 15, wherein, the temperature of the drying is 60° C.

17. The method of claim 7, wherein, the reaction temperature of the alkylation reaction is 20-30° C.

18. The method of claim 1, wherein, the addition order of the reactants for the alkylation reaction is: adding the cyclen, the acid-binding agent, the water and the $XCH_2COOR$ sequentially to the reaction system.

* * * * *